United States Patent
Darian et al.

(10) Patent No.: US 10,398,463 B2
(45) Date of Patent: Sep. 3, 2019

(54) ULTRASONIC INSTRUMENT AND METHOD FOR MANUFACTURING SAME

(71) Applicant: Misonix Incorporated, Farmingdale, NY (US)

(72) Inventors: Alexander Darian, Brightwaters, NY (US); Dan Voic, Cedar Grove, NJ (US)

(73) Assignee: MISONIX INCORPORATED, New York, NY (US)

( * ) Notice: Subject to any disclaimer, the term of this patent is extended or adjusted under 35 U.S.C. 154(b) by 923 days.

(21) Appl. No.: 13/930,148

(22) Filed: Jun. 28, 2013

(65) Prior Publication Data
US 2015/0005795 A1  Jan. 1, 2015

(51) Int. Cl.
*A61B 17/32* (2006.01)

(52) U.S. Cl.
CPC ............ *A61B 17/320068* (2013.01); *A61B 2017/320072* (2013.01); *Y10T 29/49* (2015.01)

(58) Field of Classification Search
CPC  A61B 17/320068; A61B 2017/320072; A61B 17/2202; A61B 17/22012; A61B 2017/320084; A61B 2017/22014; A61B 2017/22011; A61B 2017/00526; A61B 2017/003; A61B 2017/00292; A61B 2017/00154; A61B 2017/00141; A61B 2017/22015; A61B 2017/00331; Y10T 29/49; A61M 25/0041; A61M 25/001; A61M 25/0009
See application file for complete search history.

(56) References Cited

U.S. PATENT DOCUMENTS 4,832,683 A  *  5/1989  Idemoto ......... A61B 17/320068
                                                    604/22
5,359,996 A     11/1994  Hood
5,540,693 A  *  7/1996  Fisher ............... A61B 17/1659
                                                    606/79

(Continued)

FOREIGN PATENT DOCUMENTS

CN  201260686 Y  6/2009
CN  102105111 A  6/2011

(Continued)

OTHER PUBLICATIONS

Misonix, Inc. "Sonstar Ultrasonic Tissue Aspiration" Brochure 2010 pp. 3-4.

*Primary Examiner* — Julian W Woo
(74) *Attorney, Agent, or Firm* — R. Neil Sudol; Henry D. Coleman

(57) ABSTRACT

An ultrasonic tool or instrument has a probe shaft with a linear proximal end portion and a linear distal end portion disposed at an angle relative to one another and joined at a bend in the shaft. A coupling is provided at a proximal end of the shaft for connecting the probe to a source of ultrasonic vibrational energy. A head provided at a distal end of the shaft extends eccentrically in a transverse direction to one side of the shaft. The head has an operative tip spaced laterally from the axis and is formed with at least one cutout for reducing mass of the head and concomitantly eccentric mass of the probe. The tool or instrument has at least one interior antinode along the shaft and the bend is located substantially distally of the antinode.

12 Claims, 1 Drawing Sheet

(56) References Cited

U.S. PATENT DOCUMENTS

| | | | | |
|---|---|---|---|---|
| 5,725,495 | A * | 3/1998 | Strukel | A61M 1/0043 604/22 |
| 6,283,981 | B1 | 9/2001 | Beaupre | |
| 6,458,143 | B1 * | 10/2002 | Sugai | A61B 17/320068 606/169 |
| 6,498,421 | B1 * | 12/2002 | Oh | A61B 17/1642 310/323.12 |
| 8,100,823 | B2 * | 1/2012 | Harp | A61B 17/1624 600/104 |
| 8,512,340 | B2 * | 8/2013 | Easley | A61B 17/1659 606/79 |
| 9,907,560 | B2 * | 3/2018 | O'Neil | A61B 17/1671 |
| 10,016,208 | B2 * | 7/2018 | Gouery | A61B 17/320068 |
| 2003/0204199 | A1 | 10/2003 | Novak | |
| 2004/0006269 | A1 | 1/2004 | Novak et al. | |
| 2005/0177184 | A1 * | 8/2005 | Easley | A61B 17/1659 606/167 |
| 2006/0161189 | A1 | 7/2006 | Harp | |
| 2006/0200155 | A1 * | 9/2006 | Harp | A61B 17/1624 606/85 |
| 2006/0211943 | A1 | 9/2006 | Beaupre | |
| 2007/0015102 | A1 * | 1/2007 | Vercellotti | A61C 3/03 433/2 |
| 2007/0016236 | A1 | 1/2007 | Beaupre | |
| 2008/0058775 | A1 * | 3/2008 | Darian | A61B 17/320068 606/1 |
| 2008/0300591 | A1 * | 12/2008 | Darian | A61B 17/320068 606/41 |
| 2009/0270891 | A1 * | 10/2009 | Beaupre | A61B 17/320092 606/169 |
| 2009/0326535 | A1 * | 12/2009 | Blus | A61B 17/320068 606/80 |

FOREIGN PATENT DOCUMENTS

| | | |
|---|---|---|
| EP | 0 968 684 A1 | 1/2000 |
| JP | 63-88311 | 6/1988 |
| JP | 2000-70279 | 7/2000 |
| JP | 2005-74088 | 1/2005 |
| WO | WO8602257 A1 | 4/1986 |
| WO | WO 2003/092793 A2 | 11/2003 |

* cited by examiner

ULTRASONIC INSTRUMENT AND METHOD FOR MANUFACTURING SAME

BACKGROUND OF THE INVENTION

This invention relates to an ultrasonic tool or instrument particularly, but not exclusively, for use in medical surgical procedures. This invention also relates to an associated process for manufacturing the ultrasonic instrument or tool Ultrasonic tools have become increasingly used in surgical procedures. Ultrasonic ablation tools are recognized for their accuracy, reliability and ease of use. Ultrasonic bone cutting blades may be designed to facilitate the cutting of bone without damage to adjacent soft tissues. See U.S. Pat. No. 8,343,178. Ultrasonic debriders remove necrotic or otherwise damaged tissue without harming underlying healthy tissue. Ultrasonic instruments such as debriders can have integrated tissue treatment modalities such as high-energy electrical current transmission for cauterization (See U.S. Pat. No. 6,648,839) and low-energy electrical energy transmission for pain suppression (U.S. Patent Application Publication No. 2008/0146921) or stimulating tissue repair (U.S. Pat. No. 8,025,672).

Ultrasonic instruments can incorporate probes with bent shafts for facilitating access to troublesome locations. In some surgical procedures, it is advantageous to have the operative head or end effector portion of the probe angled to one side of the shaft to further facilitate access to a desired surgical site. Typically, in full-wave probe/handpiece assemblies, the center of the shaft bend is located at or near an interior antinode. For symmetric or mostly symmetric probe tip designs, this tends to minimize transverse vibrations and ensures viable ultrasonic operation. A problem arises, however, where the probe head is markedly asymmetric relative to the probe shaft, for example, where a probe shaft carries a highly protruding eccentric shaving head with a large unbalanced mass located off of the central axis. While such an eccentric head design is found by surgeons to be advantageous in effectively undercutting bony anatomy, allowing for deeper cutting, such eccentricity of the probe tends to produce undesirable transverse vibration.

OBJECTS OF THE INVENTION

It is an object of the present invention to provide an improved ultrasonic tool or instrument that has an eccentrically disposed head.

It is a more particular object of the present invention to provide such a tool or instrument wherein transverse vibrations owing to the eccentricity of the head are reduced.

Another object of the present invention is to provide such a tool or instrument that additionally has a bent shaft.

A further object of the present invention is to provide an associated method for manufacturing such a tool or instrument.

These and other objects of the present invention will be apparent from the descriptions and drawings herein. Although all of the objects of the invention are achieved by one or more embodiments of the invention, there is not necessarily any single embodiment that achieves all of the objects of the invention.

SUMMARY OF THE INVENTION

An ultrasonic tool or instrument in accordance with the present invention comprises a probe shaft having a proximal end portion and a distal end portion, the distal end portion having an axis of symmetry. A coupling is provided at a proximal end of the shaft for connecting the probe to a source of ultrasonic vibrational energy. A head is provided at a distal end of the distal end portion of the shaft, the head extending eccentrically in a transverse direction to one side of the shaft. The head has an operative tip spaced laterally from the axis and is formed with at least one cutout for reducing mass of the head and concomitantly the eccentric mass of the probe.

Typically, the head has a pair of opposing edges each extending at least partially transversely to the axis. In that case, the cutout is located closer to one of the edges (e.g., a proximal edge) than another of the edges (e.g., a distal edge). The purpose and effect of such a configuration are to place the cutout at a maximal distance from the longitudinal axis of the probe's distal end portion and thus maximize the reduction in transverse vibration afforded by the cutout.

The cutout in the probe head may take any form, such as a recess, a groove, a slot, or a through hole. In a preferred embodiment, the cutout is a cylindrical through hole formed by drilling. However, the cutout may take other forms, such as an oval cylinder or a polygonal recess, groove or through hole. In addition, the plane or axis of the cutout may vary. Where drilling forms the cutout, the drill may be directed through different faces or surfaces of the probe head.

Where the distal end portion of the shaft is straight or linear and the proximal end portion of the shaft is straight or linear, the distal end portion of the shaft may be connected to the proximal end portion at a bend junction or joint, the distal end portion being disposed at an angle relative to the proximal end portion. The tool or instrument has at least one interior antinode along the shaft and, pursuant to another feature of the invention, the bend junction is located substantially distally of the antinode. This unusual locating of the bend junction provides additional compensation for the eccentricity of the probe head.

Pursuant to a more particular feature of the present invention, where the tool or instrument is configured for operation with a standing wave having a predetermined wavelength, the bend junction is located distally of the interior antinode at distance therefrom of up to about a quarter of the operating wavelength.

A method of manufacturing an ultrasonic tool or instrument comprises, in accordance with the present invention, (a) providing a probe shaft with a distal end portion having an axis of symmetry, (b) forming a head at a distal end of the distal end portion of the shaft so that the head extends eccentrically in a transverse direction to one side of the distal end portion of the shaft and so that an operative tip of the head is spaced laterally from the axis, and (c) forming the head with at least one cutout for reducing mass of the head and concomitantly eccentric mass of the shaft.

The forming of the cutout in the head may be implemented by drilling the cutout in the head. Where the forming of the head includes providing the head with a pair of opposing edges each extending at least partially transversely to the axis, the forming of the cutout may include locating the cutout closer to one of the edges than another of the edges. The cutout is also spaced from the operative tip so that the cutout does not reduce the size or effective surface of the operative tip.

The method may further comprise providing the shaft with a proximal end portion continuous with the distal end portion at a bend and disposed at an angle relative to the distal end portion. In that case, the method may include forming the probe shaft so that the bend is located substantially distally of an interior antinode of the tool or instrument.

An ultrasonic tool or instrument in accordance with the present invention comprises (i) a probe shaft having a proximal end portion and a distal end portion, the distal end portion having an axis of symmetry, (ii) a coupling at a proximal end of the shaft for connecting the probe to a source of ultrasonic vibrational energy, and (iii) a head at a distal end of the distal end portion of the shaft. The head extends eccentrically in a transverse direction to one side of the shaft and has an operative tip spaced laterally from the axis. The distal end portion and the proximal end portion of the shaft are both straight or linear. Pursuant to a feature of the present invention, the distal end portion of the shaft is connected to the proximal end portion at a bend junction and is disposed at an angle relative to the proximal end portion. Moreover, where the tool or instrument has an interior antinode along the shaft, the bend junction is located substantially distally of the antinode.

Where a handpiece is connected to the shaft at the coupling, the interior antinode may be located approximately midway along a combined length of the shaft and the handpiece. In that event, the bend junction is located distally of an interior antinode at a distance therefrom of up to about half of the distance from the interior antinode to the head.

Where the tool or instrument is configured for operation with a standing wave having a predetermined operating wavelength, the bend junction is located distally of an interior antinode at a distance therefrom of up to about a quarter of the operating wavelength.

The angle between the proximal and distal end portions of the probe shaft is between 0 degrees and 15 degrees and preferably about 10 degrees or less.

Where the bend is the probe shaft has an outer or convex side on a given side of the shaft, the head typically but not necessarily protrudes from the distal end portion of the shaft on the given side thereof.

The head of the probe is preferably formed with at least one cutout for reducing mass of the head and concomitantly eccentric mass of the probe. Both the reduction in head mass afforded by the cutout and the locating of the bend forward of the interior antinode contribute to reducing unwanted transverse vibrations of the ultrasonic instrument.

A method of manufacturing an ultrasonic tool or instrument comprises, in accordance with the present invention, (1) providing a probe shaft with a distal end portion having an axis of symmetry, (2) forming a head at a distal end of the distal end portion of the shaft so that the head extends eccentrically in a transverse direction to one side of the distal end portion of the shaft and so that an operative tip of the head is spaced laterally from the axis, (3) providing the shaft with a proximal end portion continuous with the distal end portion at a bend and disposed at an angle relative to the distal end portion, and (4) forming the probe shaft so that the bend is located substantially distally of an interior antinode of the tool or instrument.

Pursuant to another feature of the present invention, where the head has a predetermined eccentric mass, the method further comprises locating the bend along the shaft in dependence on a magnitude of the eccentric mass, the location of the bend being more distal the greater the eccentric mass.

The bend is preferably located distally of an interior antinode at a distance therefrom of up to about half of the distance from the interior antinode to the head.

The head may be formed with at least one cutout for reducing mass of the head and concomitantly eccentric mass of the shaft.

Typically, the tool or instrument is configured for operation with a standing wave having a predetermined operating wavelength. The bend is disposed at a location along the shaft that is up to about a quarter of the operating wavelength from an interior antinode.

As mentioned above, both the reduction in head mass afforded by the cutout (and more particularly, the reduction in eccentric mass of the head) and the locating of the bend forward of the interior antinode contribute to reducing unwanted transverse vibrations of the ultrasonic instrument. Either the cutout or the location of the shaft bend may be sufficient in itself to reduce transverse vibrations to a manageable level. But using both approaches is optimal.

DETAILED DESCRIPTION

Figure 1:
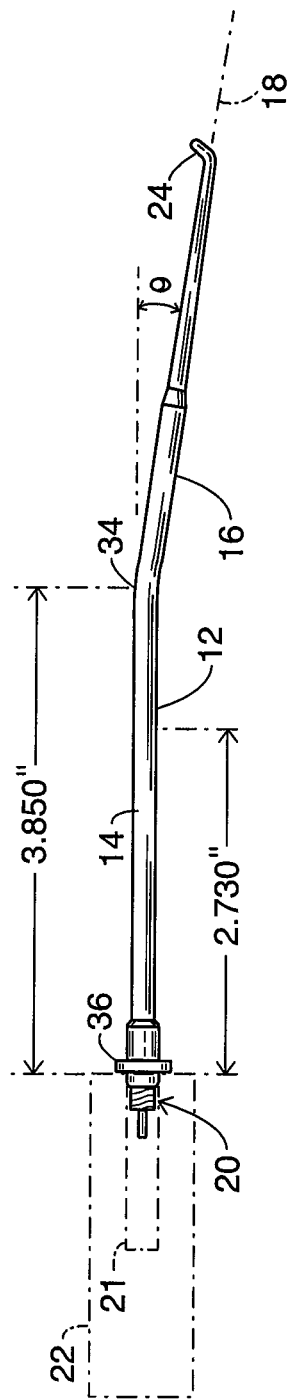
FIG. 1 is a side elevational view of an ultrasonic probe or tool in accordance with the present invention.
Figure 2:
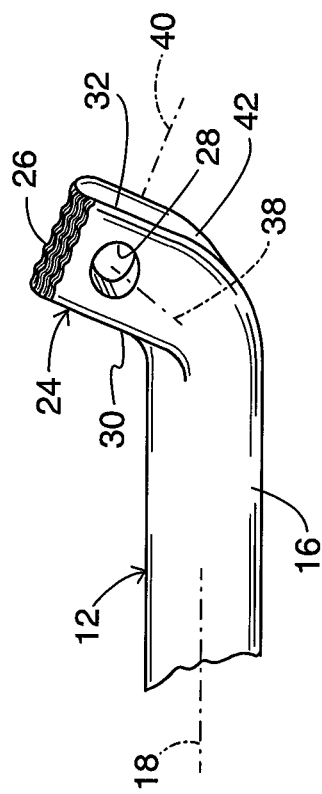
FIG. 2 is a partial perspective view of the probe of FIG. 1 on an enlarged scale.

As illustrated in the drawings, an ultrasonic tool or instrument comprises a probe shaft 12 having a proximal end portion 14 and a distal end portion 16. Distal end portion 16 has an axis of symmetry 18. A coupling 20 is provided at a proximal end of shaft 12 for connecting the probe to a source of ultrasonic vibrational energy. Typically, the source of vibration is a piezoelectric transducer stack 21 (see U.S. Pat. No. 5,371,429) disposed in an instrument handle or handpiece 22. Probe shaft 12 is mechanically connected via coupling 20 to handle 22 and operatively connected via coupling 20 to the piezoelectric transducer stack.

A head 24 is provided at a distal end of distal end portion 16 of shaft 12. Head 24 extends eccentrically in a transverse direction to one side of shaft 12. Head 24 has an operative tip or surface 26 spaced laterally from axis 18 and is formed with at least one cutout 28 for reducing the mass of the head and concomitantly the eccentric mass of the probe. Operative surface 26 may be knurled, for instance, where the ultrasonic tool or instrument is intended for use in bone abrasion.

Cutout 28 is preferably at a maximal distance from axis 18, which maximizes the reduction in transverse vibration afforded by the cutout. Accordingly, where head 24 is inclined or slanted relative to distal probe portion 16 so that the head has a pair of opposing edges 30 and 32 of the head each extending at least partially transversely to axis 18, cutout 28 is disposed closer to proximal edge 30 than to distal edge 32. Alternatively described, cutout 28 is disposed in a corner of head 24, between operative surface 26 and proximal lateral edge 30.

Cutout 28 may take any form, such as one or more recesses, grooves, slots, counterbores, etc. In the illustrated embodiment, cutout 28 is a cylindrical through hole, with an exemplary diameter of 0.047 inch. Drilling transversely to head 24 easily forms this type of cutout. Cutout 28 may take other specific forms, such as an oval cylinder or a polygonal recess, groove. Probe head 24 may be provided with more than one cutout. Drilling of probe head 24 to form cutout 28 may take place through any sutiable surface or face of the probe head, so that the orientation or axis of cutout 28 may vary from probe head to probe head. Also, cutout 28 may be formed by multiple insertions of a drill into probe head 24, along different directions, for instance, along an axis 38 and an axis 40, the latter axis extending through a face 42 of probe head 24. In brief, head 24 has a perforate portion of reduced mass and an imperforate portion without holes or recesses. The perforate portion, e.g., including cutout(s) 28 is disposed eccentrically relative to head 24, closer to proximal edge 30 than to distal edge 32 and in the corner formed by edge 30 and operative tip or surface 26, the imperforate portion being the remaining portion of head 24.

Distal end portion 16 and proximal end portion 14 of shaft 12 are both straight or linear. Distal end portion 16 is connected to proximal end portion 14 at a bend junction or joint 34. Distal end portion 16 is disposed at an angle θ relative to proximal end portion 14. Angle θ is typically between 0° and 15° and is preferably about 10° or less.

Typically, the ultrasonic instrument or tool is operated at a frequency where there is exactly one interior antinode along shaft 12 and bend junction 34 is located substantially distally of the antinode. At that typical operating frequency, there is a further antinode at the transducer in the handle 22 and another antinode at the distal end of shaft 12, at least approximate to operative tip or surface 26.

In one embodiment as depicted in the drawings, shaft 12 has a length of 7.052' inches, while head 24 has a length of up to 0.250 inch. The operating frequency is 23 kHz with an associated standing-wave or operating wavelength of 9.20 inches. There is a single interior antinode at about 2.730 inches from a flange 36 of coupling 20. Bend 34 is located 3.850 inches from flange 36. This bend location achieves stable vibration with minimal transverse and vibration-free rear handpiece housing 22, as well as acceptable tip loading. In general, bend joint or junction 34 is located beyond the interior antinode by a distance of between about up to about a quarter of the wavelength.

The reduction in the eccentric mass of head 24 afforded by cutout 28 and the locating of bend 34 forward of the interior antinode both contribute to reducing unwanted transverse vibrations of the ultrasonic instrument. While cutout 28 and the location of shaft bend 34 individually contribute to reductions in transverse vibrations, incorporating both approaches in an ultrasonic instrument is optimal.

A method for manufacturing an ultrasonic instrument concomitantly includes either the machining of cutout 28 or the providing of bend 34 at a distally shifted location or both.

In manufacturing an ultrasonic tool or instrument as described above, one provides probe shaft 12 with distal end portion 16 having axis of symmetry 18, forms head 24 at the distal end of distal shaft portion 16 so that the head extends eccentrically in a transverse direction to one side of shaft portion 16 and so that operative tip 26 is spaced laterally from axis 18, and forms head 24 with at least one cutout 28 for reducing mass of head 24 and concomitantly eccentric mass of shaft 12. Instead of or in addition to the forming of head 24 with cutout 28, one may provide shaft 12 with bend 34 at a location substantially distal of an interior antinode, for instance, by a distance of up to about a quarter of the operating wavelength.

The forming of cutout 28 is preferably implemented by drilling the cutout in head 24. Where the forming of head 24 includes providing the head with proximal edge 30 and distal edge 32, the forming of cutout 28 preferably includes locating the cutout closer to proximal edge 30 than to distal edge 32, which maximizes eccentric mass reduction per unit removed mass. Cutout 28 may be spaced from operative tip 26 so that the cutout does not reduce the size or effective surface of the operative tip. It is to be noted, however, that cutout 28 may take the form of a slot cut into head 24 through operative surface 26, which would reduce the effective area of the surface. Cutout 28 may take other forms, such as one or more grooves or recesses.

Where shaft 12 is provided with proximal end portion 14 and distal end portion 16 continuous with one another at bend junction 34 and disposed at angle θ relative to one another and where shaft 12 is formed so that bend 34 is located substantially distally of an interior antinode of the tool or instrument, the method may further comprise locating the bend along the shaft in dependence on a magnitude of the eccentric mass (generally, but not exclusively, the mass of head 24). The location of bend 34 is more distal, the greater the eccentric mass. As indicated above, bend 34 is preferably located at a distance from an interior antinode that is up to about, or less than, half of the distance from the interior antinode to head 24. Concomitantly, a node is located between bend 34 and the head 24. Typically, the tool or instrument is configured for operation with a standing wave having a predetermined wavelength. Bend 34 is disposed at a distance from the interior antinode that is up to about a quarter of the wavelength.

As mentioned above, both the reduction in the mass of head 24 afforded by cutout 28 and the locating of bend 34 forward of an interior antinode contribute to reducing unwanted transverse vibrations of the ultrasonic instrument. Either cutout 28 or the location of the shaft bend 34 may be sufficient in itself to reduce transverse vibrations to a manageable level. Generally, without a distally displaced shaft bend, the volume of cutout 28 must be greater to ensure adequate eccentric mass reduction. Concomitantly, where cutout 28 is omitted or reduced in size, bend 34 must be shifted further distally in order to provide adequate reduction of transverse vibration. Accordingly, using both approaches is optimal.

Although the invention has been described in terms of particular embodiments and applications, one of ordinary skill in the art, in light of this teaching, can generate additional embodiments and modifications without departing from the spirit of or exceeding the scope of the claimed invention. Where cutout 28 takes the form of a slot, the slot may extend parallel to operative surface 26 toward edge 32. Where cutout takes the form of one or more recesses, the recesses may extend inwardly into opposing lateral surfaces of head 24.

The present invention may be useful where an ultrasonic probe is used in an application other than surgery, for instance, in cleaning hard-to-reach surfaces in industrial facilities.

The probe tip, i.e., head 24 and operative surface 26, may have a different shape, such as a point or spatula-like configuration. While in the illustrated embodiment head 24 is disposed on a convex side of shaft 12, there are likely to be applications in which head 24 protrudes in the opposite direction, towards the concave side of shaft 12, or in another direction.

Accordingly, it is to be understood that the drawings and descriptions herein are proffered by way of example to facilitate comprehension of the invention and should not be construed to limit the scope thereof.

What is claimed is:

1. An ultrasonic tool or instrument, comprising:
   a shaft consisting of exactly two linear or straight portions including a proximal end portion and a distal end portion disposed at an angle relative to one another and connected to one another at a bend junction, said distal end portion having an axis of symmetry;

a coupling at a proximal end of said shaft for operatively connecting said shaft to a source of ultrasonic vibrational energy; and a head at a distal end of said distal end portion of said shaft, said head extending eccentrically in a transverse direction to one side of said distal end portion of said shaft, said head having an operative tip or surface spaced laterally from said axis of symmetry, said head and said distal end portion of said shaft being disposed entirely to one side of a longitudinal axis of said proximal end portion of said shaft, said head being formed with exactly one hole or recess for reducing mass of said head and concomitantly eccentric mass of the shaft, said head having a first edge forming a corner with said operative tip or surface, said first edge extending only on said one side of said distal end portion of said shaft, said head having a second edge disposed partially on said one side of said distal end portion of said shaft, said second edge extending from one side of said axis of symmetry to an opposite side of said axis of symmetry, said hole or recess being disposed eccentrically relative to said head, said head having a distal end portion extending from said first edge to said second edge and including said operative tip or surface and said exactly one hole or recess, said distal end portion of said head being disposed to said one side of said, axis of symmetry.

2. The tool or instrument defined in claim 1 wherein said hole or recess is a cylindrical through hole.

3. The tool or instrument defined in claim 1 wherein said tool or instrument has an interior antinode along said shaft, said bend junction being located substantially distally of said antinode.

4. The tool or instrument defined in claim 3 wherein said tool or instrument is configured for operation with a standing wave having a predetermined wavelength, said bend junction being at a location along said shaft distal of said interior antinode by a distance of up to about a quarter of said predetermined wavelength.

5. The tool or instrument defined in claim 1 wherein said hole or recess is disposed at a maximal distance from said axis of symmetry.

6. The tool or instrument defined in claim 1 wherein said shaft and said head are configured to deliver ultrasonic vibrational energy to said operative tip or surface for application to a target surface via said operative tip or surface.

7. An ultrasonic tool or instrument, comprising:
a shaft consisting of exactly two linear or straight portions including a proximal end portion and a distal end portion disposed at an angle relative to one another and connected to one another at a bend junction, said distal end portion having an axis of symmetry;

a coupling at a proximal end of said shaft for connecting the shaft to a source of ultrasonic vibrational energy; and a head at a distal end of said distal end portion of said shaft, said head extending eccentrically in a transverse direction to one side of said distal end portion of said shaft, said head having an operative tip or surface spaced laterally from said axis of symmetry, said head and said distal end portion of said shaft being disposed entirely to one side of a longitudinal axis of said proximal end portion of said shaft, said tool or instrument having exactly one interior antinode along said shaft, said bend junction being located substantially distally of said antinode, said bend junction being located at a distance from said interior antinode that is less than half of the distance from said interior antinode to said head, a node being located along said distal end portion of said shaft between said bend junction and said head wherein said head is formed with at least one hole or recess for reducing mass of said head and concomitantly eccentric mass of the shaft, said at least one hole or recess being disposed laterally from said axis of symmetry.

8. The tool or instrument defined in claim 7, further comprising a handpiece connected to said shaft at said coupling, said interior antinode being located approximately midway along a combined length of said shaft and said handpiece.

9. The tool or instrument defined in claim 7 wherein said tool or instrument is configured for operation with a standing wave having a predetermined wavelength, said bend junction being located at a distance along said shaft of up to about a quarter of said wavelength from said interior antinode.

10. The tool or instrument defined in claim 7 wherein said angle is between 0 degrees and 15 degrees.

11. The tool or instrument defined in claim 7 wherein said bend has an outer or convex side on a given side of said shaft, said head protruding from said distal end portion of said shaft on said given side thereof.

12. An ultrasonic tool or instrument, comprising:
a shaft consisting of exactly two linear or straight portions including a proximal end portion and a distal end portion disposed at an angle relative to one another and connected to one another at a bend junction, said distal end portion having an axis of symmetry;

a coupling at a proximal end of said shaft for operatively connecting said shaft to a source of ultrasonic vibrational energy; and a head at a distal end of said distal end portion of said shaft, said head extending eccentrically in a transverse direction to one side of said distal end portion of said shaft, said head having an operative tip or surface spaced laterally from said axis of symmetry, said head having a perforate portion of reduced mass and an imperforate portion without holes or recesses, said operative tip or surface being a knurled surface, said head and said distal end portion of said shaft being disposed entirely to one side of a longitudinal axis of said proximal end portion of said shaft, said head having a first edge forming a corner with said operative tip or surface, said first edge extending only on said one side of said distal end portion of said shaft, said head having a second edge disposed partially on said one side of said distal end portion of said shaft, said second edge extending from one side of said axis of symmetry to an opposite side of said axis of symmetry, said perforate portion being disposed eccentrically relative to said head, said imperforate portion being a remaining portion of said head, said head having a distal end portion extending from said first edge to said second edge and including said operative tip or surface and said perforate portion, said distal end portion of said head being disposed completely to said one side of said axis of symmetry.

* * * * *